US011482329B2

(12) United States Patent
Albert et al.

(10) Patent No.: US 11,482,329 B2
(45) Date of Patent: Oct. 25, 2022

(54) MEDICAL AUDIO ALARM DISTRIBUTED DETECTION AND ALERT SYSTEM (71) Applicant: Government of the United States as represented by the Secretary of the Air force, Kirtland AFB, NM (US)

(72) Inventors: Michael D Albert, Las Cruces, NM (US); David R Desrochers, Fredericksburg, VA (US); Christopher Valerino, Liverpool, NY (US)

(73) Assignee: Government of the United States as represented by the Secretary of the Air Force, Kirtland AFB, NM (US)

( * ) Notice: Subject to any disclaimer, the term of this patent is extended or adjusted under 35 U.S.C. 154(b) by 0 days.

(21) Appl. No.: 17/190,970

(22) Filed: Mar. 3, 2021

(65) Prior Publication Data
US 2021/0280310 A1   Sep. 9, 2021

Related U.S. Application Data (60) Provisional application No. 62/984,326, filed on Mar. 3, 2020.

(51) Int. Cl.
*H04R 29/00* (2006.01)
*G16H 40/67* (2018.01)
(Continued)

(52) U.S. Cl.
CPC .......... *G16H 40/67* (2018.01); *G08B 21/18* (2013.01); *G10L 25/51* (2013.01); *H04R 1/08* (2013.01);
(Continued)

(58) Field of Classification Search
CPC ...................................................... H04R 29/00
See application file for complete search history.

(56) References Cited

U.S. PATENT DOCUMENTS 7,155,681 B2    12/2006  Mansour et al.
11,143,739 B2 *  10/2021  Janssen ................. H04R 1/08
(Continued)

FOREIGN PATENT DOCUMENTS

WO    2012092567    4/2014

OTHER PUBLICATIONS

Microchip, "Advanced Stand-Alone Li-Ion/Li-Polymer Battery Charge Management Controller with Autonomous AC Adapter or USB Port Source Selection," (2015) available at http://ww1.microchip.com/downloads/en/DeviceDoc/20002071C.pdf, accessed Mar. 3, 2021.

(Continued)

*Primary Examiner* — Olisa Anwah
(74) *Attorney, Agent, or Firm* — AFNWC/JA; David L. Narciso (57) ABSTRACT A system for detecting medical audio alarms. The system includes a detector and a server. The detector further comprises a microphone that is configured to receive a sound of the alarm; a microcontroller configured to determine an alarm pattern from the sound and to compare the determined alarm pattern to a plurality of patterns stored in a memory to identify a cause of the alarm; and a network interface configured to transmit the cause of the alarm. The server is configured receive the cause of the alarm and provide notification of the cause of the alarm.

20 Claims, 8 Drawing Sheets (51) Int. Cl.
  *H04R 1/40* (2006.01)
  *H04R 3/00* (2006.01)
  *H04R 1/08* (2006.01)
  *G08B 21/18* (2006.01)
  *G10L 25/51* (2013.01)

(52) U.S. Cl.
  CPC .............. *H04R 1/406* (2013.01); *H04R 3/005* (2013.01); *H04R 2201/401* (2013.01)

(56) References Cited

U.S. PATENT DOCUMENTS

| | | | |
|---|---|---|---|
| 2013/0154823 A1 | 6/2013 | Ostrer et al. | |
| 2016/0005301 A1* | 1/2016 | Mason | H04L 67/26 709/206 |
| 2018/0158288 A1* | 6/2018 | Logan | G08B 1/08 |
| 2021/0020018 A1* | 1/2021 | Kim | G08B 1/08 |
| 2021/0034732 A1* | 2/2021 | Fong | G06F 9/445 |

OTHER PUBLICATIONS

Freescale Semiconductor, Inc., "Kinetis KL25 Sub-Family," (2014) available at https://cache.nxp.com/files/32bit/doc/data_sheet/KL25P80M48SF0.pdf, accessed Mar. 3, 2021.

Ess, D.V., "Use Software Filters to Reduce ADC Noise," (2008) available at http://electronicdesign.com/analog/use-software-filters-reduce-adc-noise, accessed Mar. 3, 2021.

Chatterjee, K., "A simple digital low-pass filter in C," WordPress (2015) available at https://kiritchatterjee.wordpress.com/2014/11/10/a-simple-digital-low-pass-filter-in-c/, accessed Mar. 3, 2021.

Ren, M. et al., "Performance analysis of multiple sparse source localization with triangular pyramid microphone array in noise environment," 2012 IEEE International Conference on Signal Processing, Communication and Computer, 315-319.

Ren, M. et al., "A novel multiple sparse source localization using triangular pyramid microphone array," IEEE Singal Processing Letters (2012) vol. 19, 83-86.

* cited by examiner

MEDICAL AUDIO ALARM DISTRIBUTED DETECTION AND ALERT SYSTEM

Pursuant to 37 C.F.R. § 1.78(a)(4), this application claims the benefit of and priority to prior filed Provisional Application Ser. No. 62/984,326, filed Mar. 3, 2020, which is expressly incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to medical alerts and, more particularly, to audio alerts associated with medical alerts.

BACKGROUND OF THE INVENTION

A conventional hospital patient room 10 includes a few standard devices: a rolling bed 12 having an adjustable mattress 14 and side rails 16, an IV pump 18 secured to a stand 20 that also supports a IV bag 22 containing a fluid 24, and a vital signs monitor 26 that is configured to measure at least heart rate, blood pressure, and SpO2. Other devices may be included, depending on the type of care required by the patient and shown exemplarily shown in FIG. 1, may include compression socks device 28 and a ventilator 30. However, this should not be considered to be an exhaustive listing of potential devices found in a hospital room 10.

Figure 1:
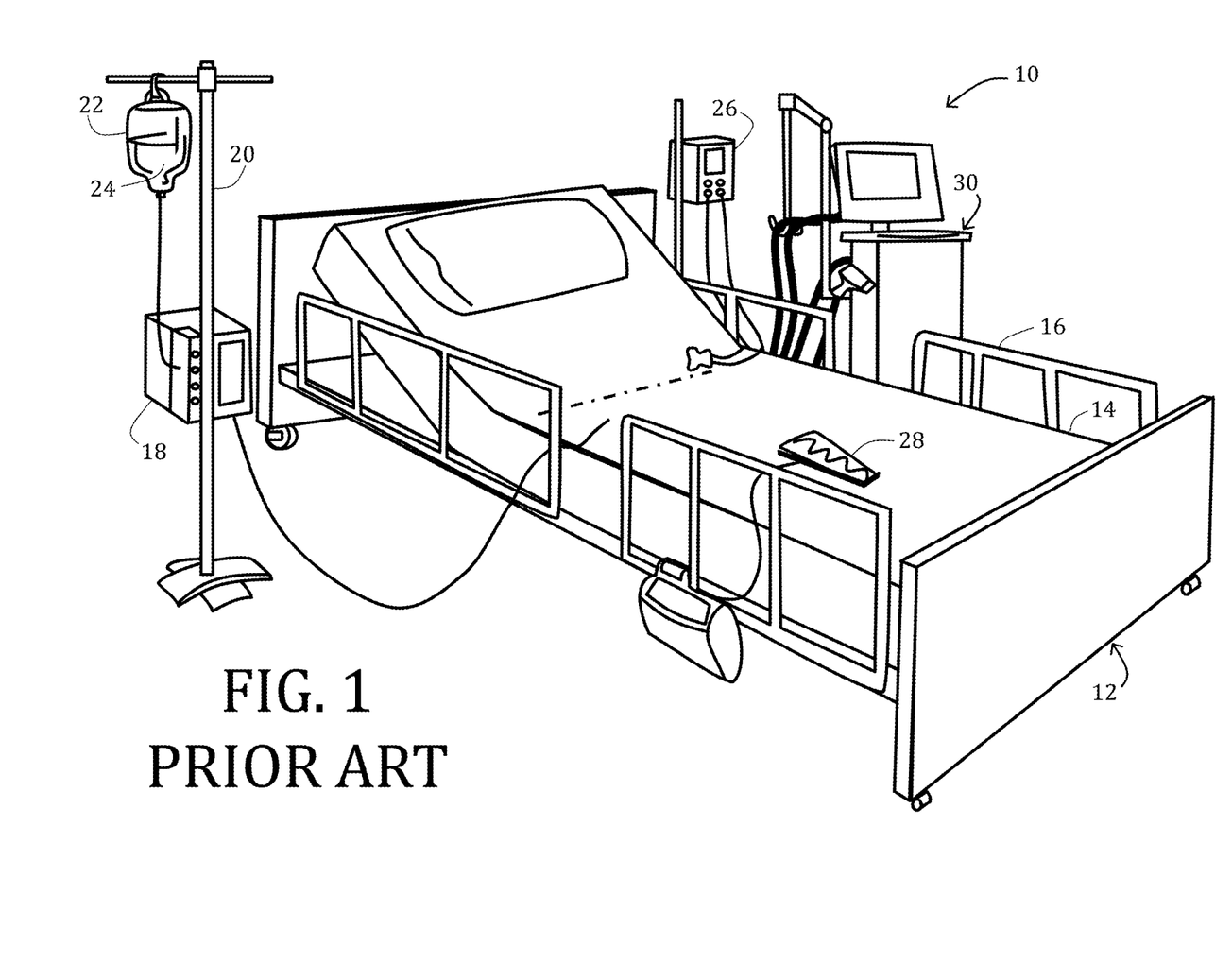
FIG. 1 is a side elevational diagram of a conventional hospital room according to the prior art.

Many of the devices found within the hospital room 10 incorporate at least one sensor configured to detect a physiological parameter of the patient or an operational parameter of the item itself. For instance, the rolling bed 12 may include a weight sensor (not shown) for detecting weight, i.e., whether patient is in the bed; the IV pump 18 may include a sensor for detecting low power supply (whether battery or disconnected from power outlet), a sensor for detecting pump malfunction, and a sensor for detecting low fluid levels within the IV bag 22; the vital signs monitor 26 may include a sensor for detecting lower power supply (whether battery or disconnected from power outlet), a sensor for detecting malfunction of the monitor 26, a sensor for detecting blood pressure, a sensor for detecting heart rate, and a sensor for detecting blood oxygen saturation. Some devices within the room may have an alarm that is associated with all sensors of that device—that is, the device will produce one alarm for any triggered sensor. Other devices may have distinct alarms associated with different sensors. For example, the vital signs monitor 26 may have a first alarm pattern associated with the detection of low power and a second alarm pattern associated with the detection of low blood pressure measurements. Therefore it is possible that each hospital room 10 can produce tens to hundreds of alarms per hospital staff shift. The sheer number of alarms that can lead to alarm fatigue, which is a sensory overload that occurs when hospital staff is exposed to an excessive number of alarms that result in desensitization.

Conventional solutions to alarm fatigue include the directing of all alarms to a telecommunications system or a portable computing device so that one user can manage alarms. However, the likelihood of false alarms or misinterpretation of alarms exists.

There remains a need for a device or system that can detect alarms, locate and process the type of alarm, facilitate triaging alarms so as to reduce the sensory overload associated with alarm fatigue, and be adaptable for use with any medical device having an alarm.

SUMMARY OF THE INVENTION

The present invention overcomes the foregoing problems and other shortcomings, drawbacks, and challenges of managing patient alert systems. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention a system for detecting medical audio alarms includes a detector and a server. The detector further comprises a microphone that is configured to receive a sound of the alarm; a microcontroller configured to determine an alarm pattern from the sound and to compare the determined alarm pattern to a plurality of patterns stored in a memory to identify a cause of the alarm; and a network interface configured to transmit the cause of the alarm. The server is configured to receive the cause of the alarm and to provide notification of the cause of the alarm.

Another embodiment of the present invention is directed to a system for detecting medical audio alarms and includes a plurality of detectors and a server. Each detector of the plurality includes a microphone that is configured to receive a sound of the alarm; a microcontroller configured to determine an alarm pattern from the sound and to compare the determined alarm pattern to a plurality of patterns stored in a memory to identify a cause of the alarm; and a network interface configured to transmit the cause of the alarm. The server is configured receive the cause of the alarm and to provide notification of the cause of the alarm. The server is also configured to compare the determined alarm pattern of the first detector of the plurality to the determined alarm pattern of the second detector of the plurality.

Still another embodiment of the present invention is for a system for monitoring a medical device alarm. The system includes a detector, a database, a processor, and a server. The detector includes a microphone configured to receive a sound of the alarm; a microcontroller configured to convert the sound of the alarm to a digital waveform; and a network interface configured to transmit the digital waveform. The database includes a library of waveforms, and each of the waveforms of the library corresponds to an alarm waveform of a medical device. The processor compares the digital waveform from the detector to waveforms of the library of the database to identify a cause of the alarm. The server distributes the cause of the alarm, provides notification of the cause of the alarm, or both.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 2:
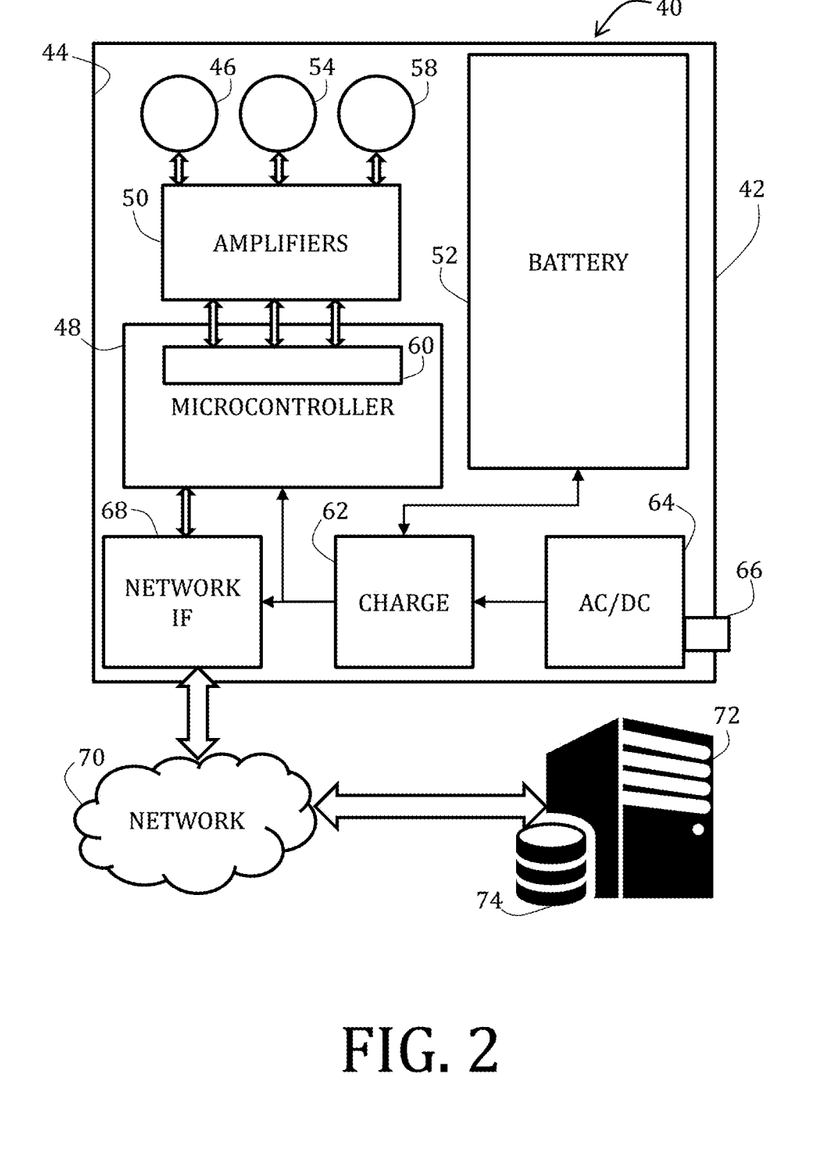
FIG. 2 is a diagrammatic view of a device and system for managing patient alert systems according to and embodiment of the present invention.

Referring now to FIG. 2, a diagrammatic, cross-sectional view of a detector 40 configured to detect, triage, and communicate audio alarms associated with a medical sensor according to an embodiment of the present invention is shown. The detector 40 is configured to be attached or otherwise mounted onto a device 12, 18, 26, 28, 30 (FIG. 1) having a medical sensor and an alarm without a need for modifying or electronically coupling to the device 12, 18, 26, 28, 30 (FIG. 1) itself. In this way the detector 40 may include a casing 42 that encloses electronic components described below therein. The casing 42 may be constructed from medical grade plastics such as polypropylene, acetal, PETG, and so forth and incorporate a hook, and adhesive strip, or other like mechanisms for attaching the detector 40 to the medical sensor device 12, 18, 26, 28, 30 (FIG. 1).

An interior 44 of the casing 42 surrounds and encloses a microphone 46 and a microcontroller 48 operably coupled to the microphone 46. Optionally, an amplifier 50 maybe coupled to the microphone 46 to improve signal-to-noise, a power supply 52 incorporated for minimizing or eliminating dependence on an external power source (not shown), may be included in the interior 44 of the casing 42.

The microphone 46 may be unidirectional or omnidirectional and may vary in number and arrangement. According to one embodiment of the present invention, a single, unidirectional microphone 46 may be included, which provides the benefit of simplicity in design and use (i.e., if positioned close to and in a direction of a particular alarm, then a likelihood of false detection is minimized); however, such design does not accommodate a plurality of locations. That is, a single omnidirectional microphone 46 would reduce the requirement of having precise alignment with a direction of the alarm, but such design could lead to false detection as any alarm within an area may be detected.

Figure 3:
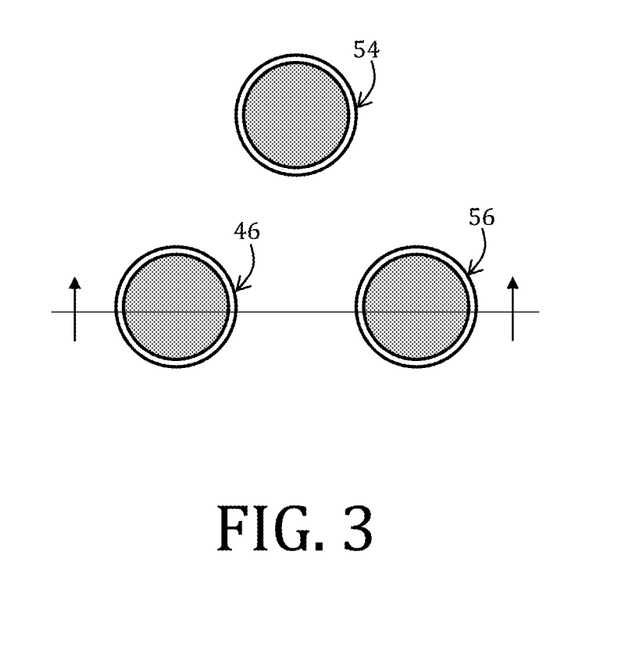
FIG. 3 is a diagrammatic view of an arrangement of microphones for the device of FIG. 2 according to an embodiment of the present invention.
Figure 3A:
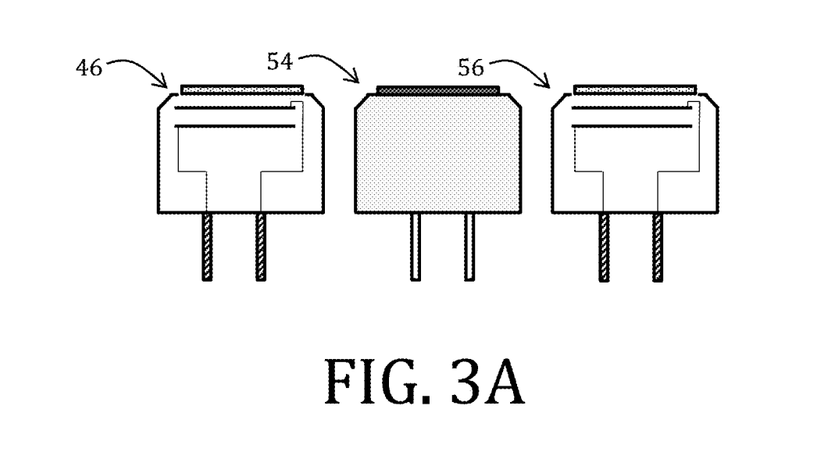
FIG. 3A is a cross-sectional view taken along the line A-A in FIG. 3.

More robust embodiments of the present invention incorporate a plurality of omnidirectional microphones 46, 54, 56 that may be used for triangulating a direction of the alarm. One suitable, omnidirectional microphone for the embodiments of the invention may include, for example, those manufactured by CUI devices. The three omnidirectional microphones 46, 54, 56 may be arranged in a planar triangle, as shown in FIGS. 3 and 3A, which would improve accuracy by enabling triangulation; however, the planar arrangement limits triangulation to a two-dimensional plane.

Figure 4:
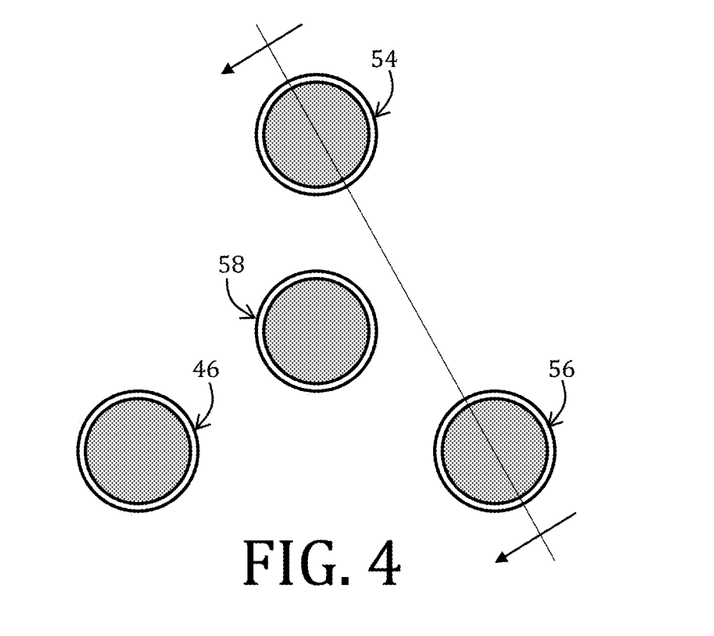
FIG. 4 is a diagrammatic view of an arrangement of microphones for the device of FIG. 2 according to another embodiment of the present invention.
Figure 4A:
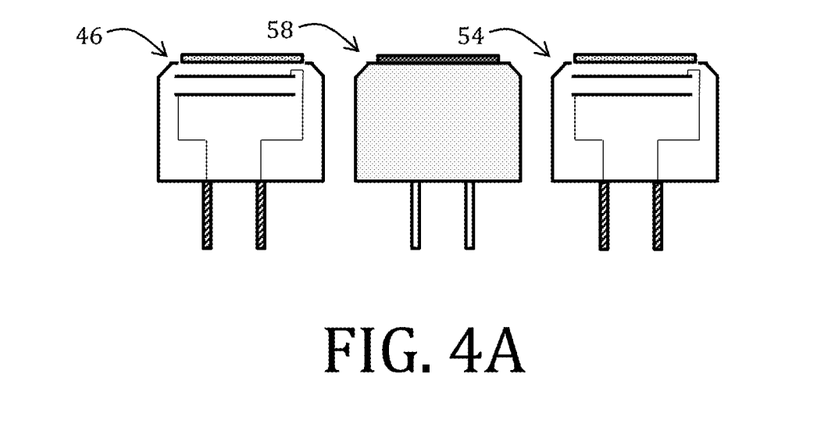
FIG. 4A is a cross-sectional view taken along the line A-A in FIG. 4.

FIGS. 4 and 4A illustrate a three-dimensional, pyramidal arrangement of four microphones 46, 54, 56, 58 that would still further improve triangulation capabilities. Such an arrangement facilitates the use of triangulating software algorithms. Two exemplary software algorithms suitable for use with embodiments of the present invention may include those described in REN et al., "A novel multiple sparse source localization using triangular pyramid microphone array," IEEE, Vol. 19 (2012) 83-86 and REN et al., "Performance analysis of multiple sparse source localization with triangular pyramid microphone array in noise environment," IEEE Xplore, (2012). The teachings of both of this reference are herein incorporated by reference, each in its entirety. According to the incorporated references, triangulation may be possible for pyramidal arrangement that is less than 21 $cm^3$ in volume (for example, 2.6 cm×2.6 cm×3 cm). As a result, pyramidal arrangement may be 21 $cm^3$ in volume or larger.

Referring again to FIG. 2, sound reaching the microphone 46, 54, 56 may be optionally directed to the amplifier 50 for purposes of improving the signal-to-noise ratio. According to one embodiment, a variable resistor 60 may be used to control the gain on all of the microphones 46, 54, 56. The microcontroller 48 is operably coupled to and controls the variable resistor 60, which modulates the amplitude of the input received sampling.

The microcontroller 48 may be any suitable microprocessor that is capable of the necessary processing speeds. For example, presuming dimensions of 3 cm (length, width, and height) pyramidal arrangement of the four microphones 46, 54, 56, 58 and a speed of sound being approximately 340 m/s (at sea-level), then the maximum delay between any two microphones 46, 54, 56, 58 of the pyramidal arrangement (FIG. 4) would be about 88.24 μs. This time delay requires the microprocessor accommodate for a sufficiently fast sample time to perceive a difference between the inputs of the microphones 46, 54, 56, 58 so as to detect a phase-shift. This requires at least a sampling rate of 11.333 KHz. This sampling rate is easily within reach of a simple microcontroller 48, such as the KL25 or FRDM-KL46Z, which is configured to continuously sample at up to 818.330 kilosamples per second. Various embodiments may require different levels of dynamic memory associated with the particular microcontroller 48.

The microcontroller 48, amplifier 50, microphone(s) 46, 54, 58, and other components of the detector 40 may be powered by way of the battery 52, which may be operably coupled to the powered components by a charge chip 62.

The battery 52 may be rechargeable (lithium ion, nickel-metal hydride, or nickel-cadmium, for example) or disposable (alkaline, zinc-carbon, lithium, mercury oxide, silver oxide, zinc-air, for example). If the battery 52 is rechargeable, then the charge chip 62 may be operably coupled to an AC-to-DC converter 64, which may include a port 66 extending through the casing 42 and configured to receive a charging plug (not shown). Alternatively, and according to some embodiments, the battery 52 may be replaceable. Accordingly, the casing 42 may include a removable cover proximate to a position of the battery 52 within the casing 42. The form of the battery 52 may vary as well. For example, a conventional AA type battery simplifies implementation and maintenance.

Figure 5:
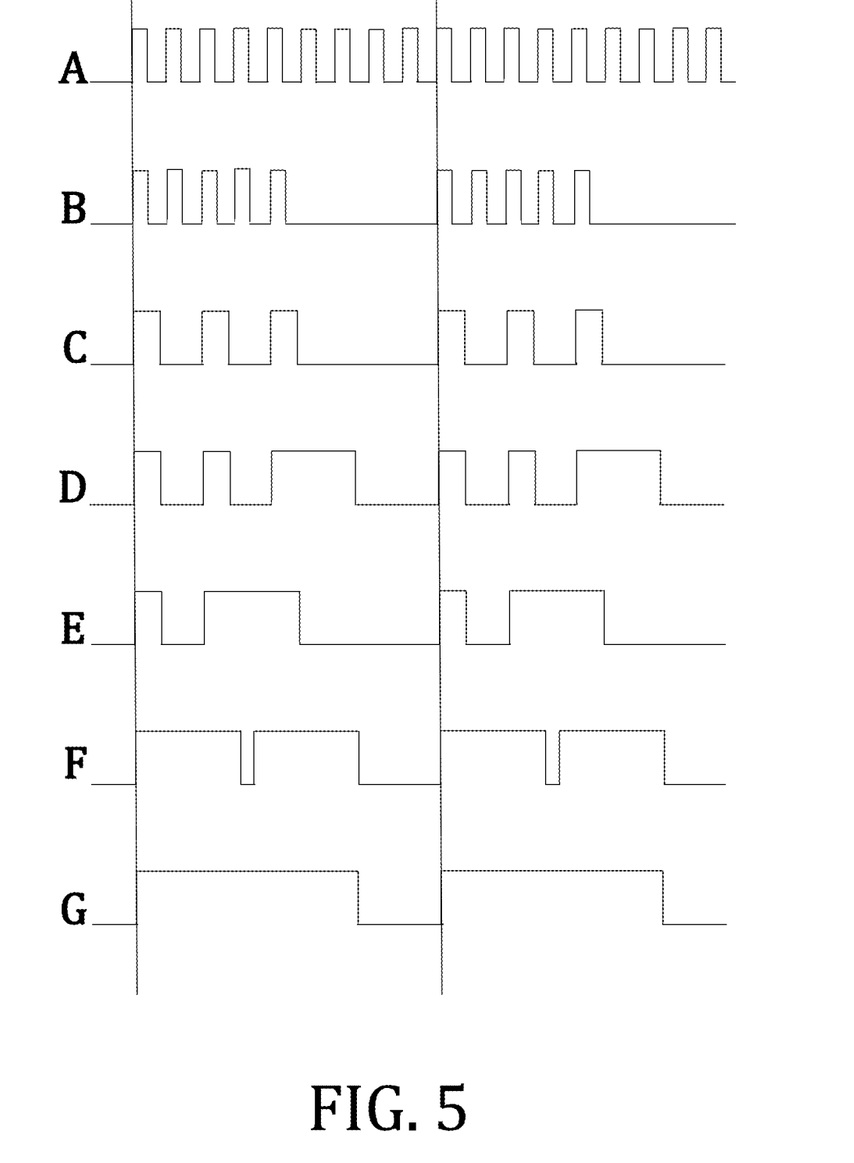
FIG. 5 illustrates seven exemplary alarm patterns that may be discernable by the device and system according to embodiments of the present invention.

With reference still to FIG. 2, amplified sound received at the microcontroller 48 may be processed to determine a pattern of the alarm. FIG. 5 illustrates seven, exemplary and different alarms patterns that may be suitable for use with embodiments of the present invention. For example, pattern A may be associated with the IV pump 18 (FIG. 1), pattern B may be associated with low pulse ox level detection by the vital signs monitor 26 (FIG. 1), pattern C may be associated with a lower power detection of the IV pump 18 (FIG. 1), and so forth. It should be noted that pattern recognition does not necessarily include further distinction by frequency of each pulse; however, other embodiments not illustrated here could include such further distinction.

The microcontroller 48 may incorporate a memory (not shown) having information, data, a look-up table, or other similar organizational structure configured to match patterns of alarms with the type of alarm, the medical device that is generating the alarm, an emergency level associated with the alarm, and combinations thereof. Once the microcontroller 48 correlates the pattern to the alarm, the microcontroller 48 may then transmit the detected pattern, nature of the alarm, the emergency level, or combinations thereof to a user by way of a network interface 68 and a network 70.

By transmitting the pattern, the associated type of alarm, or the emergency level of the alarm, the system is designed to minimize network traffic (low bandwidth data transmission), preserve power, and increase medical information transmission safety. This information, passes via the network 70 to a server 72, a database 74, or a user device (not shown).

According to some embodiments of the present invention, the server 72 may include a frontend component and a backend component. The frontend component may be configured to handle requests and to present the requests via a website; the backend component may be configured to manage data storage and real-time updating of the frontend component. The server 72 further may include a web server that is configured to provide the alert notifications (for example, by Asynchronous Javascript And XML—AJAX). For some embodiments, the web server may also be used to configure the detectors 40. The server 72 may alternatively provide the alert notifications to a hospital staff call system, a computing device located at a nurses' station, or other telecommunication systems (such as a pager, a smart phone, and so forth).

Figure 6:
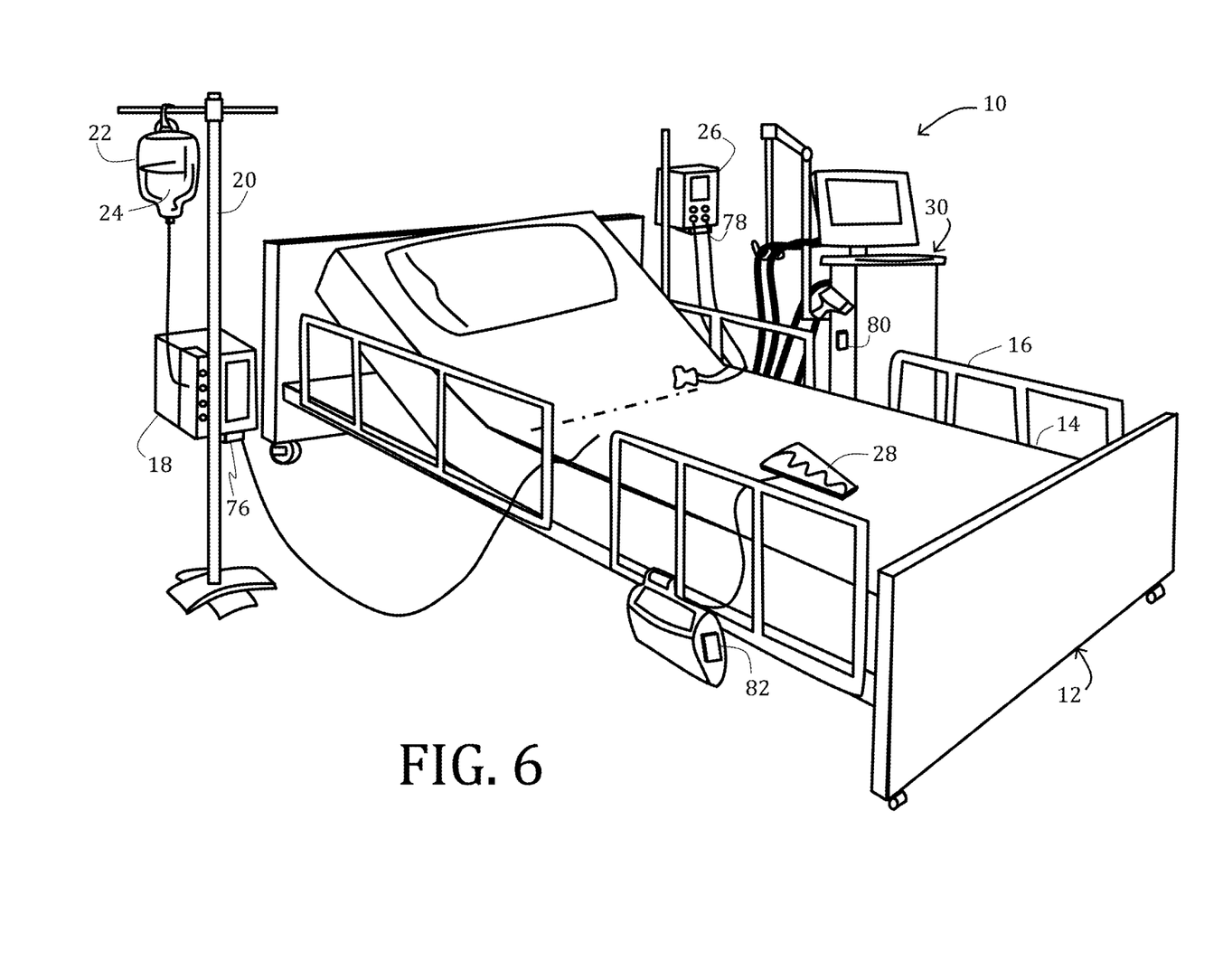
FIG. 6 illustrates a hospital room that is similar to FIG. 1 but incorporating a system for managing patient alert systems according to an embodiment of the present invention.

Referring now to FIG. 6, the hospital patient room 10 of FIG. 1 is shown but further includes a plurality of detectors 76, 78, 80, 82 configured for detecting, triaging, and communicating audio alarms associated with a medical sensor according to an embodiment of the present invention is shown. In particular, a first detector 76 is operably coupled to the IV pump 18, a second detector 78 is operably coupled to the vital signs monitor 26, a third detector 80 is operably coupled to the ventilator 30, and a fourth detector 82 is operably coupled to the compression socks device 28.

According to some embodiments of the present invention, each of the first, second, third, and fourth detectors 76, 78, 80, 82 may include a unique identifier (alpha-numeric, bar code, QR code, or RFID) such that hospital staff may associate that detector 76, 78, 80, 82 to a particular medical device 18, 26, 28, 30. Still other embodiments may further permit hospital staff to associate each detector 76, 78, 80, 82 operably coupled to a particular medical device 18, 26, 28, 30 to a particular patient room or patient bed if there is more than one patient per room. Still other embodiments of the present invention may incorporate a data port (such as USB) into the detector 76, 78, 80, 82 such that the device may be directly hard-wired into the network or into the particular device 18, 26, 28, 30 for which it is operably coupled.

When a plurality of detectors 76, 78, 80, and 82 is used, and according to another embodiment of the present invention, and when an alarm is detected by the microphone 46 (FIG. 2) of the first detector 76, the server 72 may inquire as to whether the microphone 46 (FIG. 2) of at least one of the second detector 78, the third detector 80, or the fourth detector 82 also detected the same alarm. Using the relative location of the first and second detectors 76, 78, the server 72 may be used to triangulate a source of the alarm, which may be used to confirm which medical device 18, 26, 28, 30 sounded the alarm. Such information may also be used in determining which medical device 18, 26, 28, 30 associated with which patient sounded the alarms when multiple patients reside within the same hospital room 10.

Figure 7:
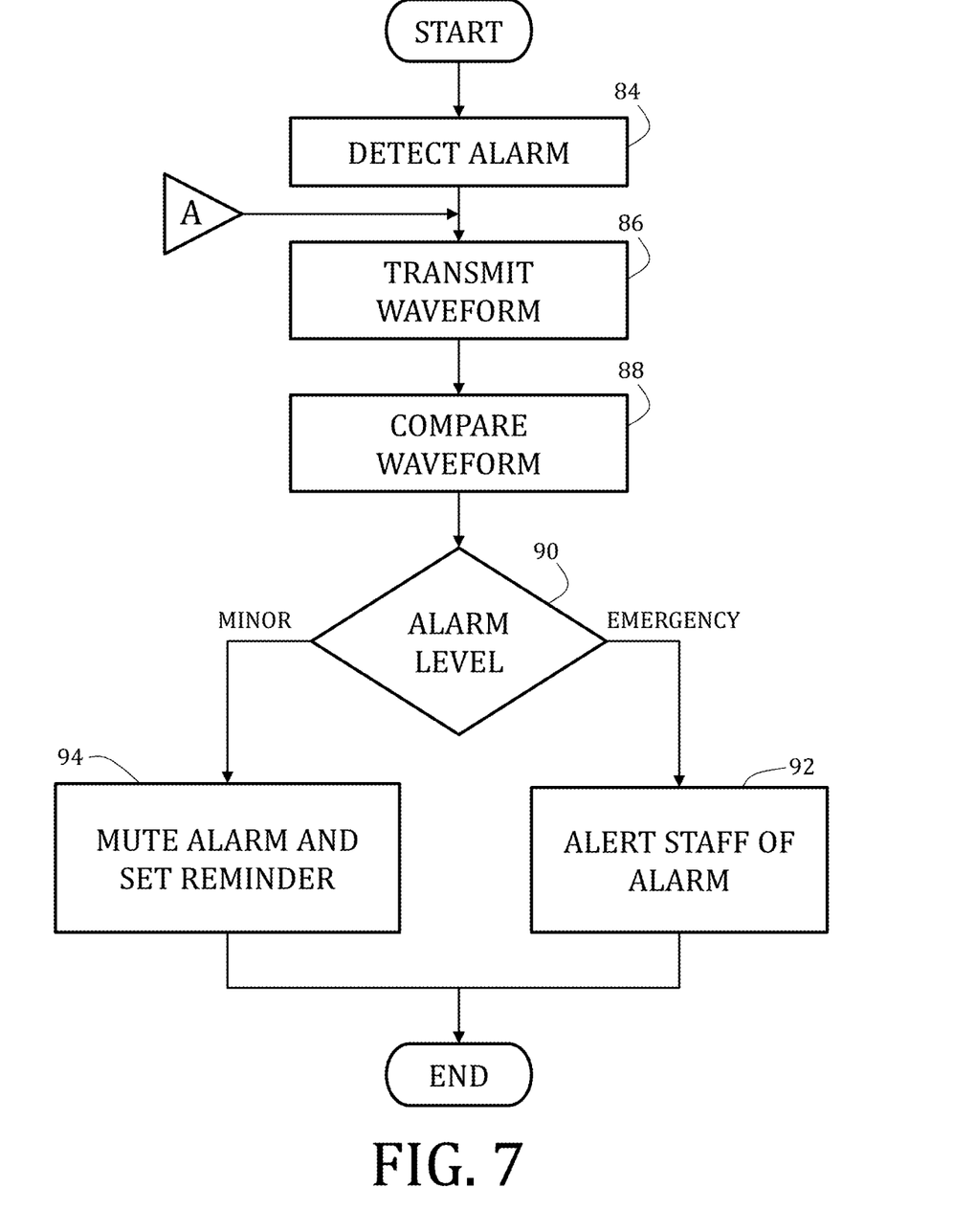
FIG. 7 is a flowchart illustrating a method of managing patient alert systems according to an embodiment of the present invention.

Referring once again to FIGS. 2 and 6 and now also to FIG. 7, a method of detecting, triaging, and communicating audio alarms associated with a medical sensor according to another embodiment of the present invention is shown. As was noted previously, sound reaching the microphone 46, 54, 56 may be optionally directed to the amplifier 50 for purposes of improving the signal-to-noise ratio. According to one embodiment, a variable resistor 60 may be used to control the gain on all of the microphones 46, 54, 56. The microcontroller 48 is operably coupled to and controls the variable resistor 60, which modulates the amplitude of the input received sampling. However, according to this particular embodiment, the microcontroller 48 is configured to convert the alarm sound from an analog signal to a digital signal. The digital signal may then be transferred to the networked devices (including, for example, the server 72 or database 74) by way of the network interface 68 and the network 70.

According to this particular embodiment, the database 74, the server 72, or both may include, stored therein, a library comprising a plurality of digital waveforms where each digital waveform is a representation of an alarm produced by a particular medical device. For example, one digital waveform of the plurality may be correlated to a low blood pressure alarm associated with the vital signs monitor 26; a second digital waveform may be correlated to low blood oxygen saturation level alarm of the vital signs monitor 26; a third digital waveform may be correlated to a low power warning alarm of the vital signs monitor 26. It is presumed that the first, second, and third digital waveforms are distinct in tone or frequency, pattern, duty cycle, or combinations thereof. As such, the database 74 may include waveforms associated with various alarms of each medical device and for various brands of medical sensor.

As such, when the second detector 78 of the vital signs monitor 26 detects an alarm (Block 84), the analog signal is converted to a digital waveform by the microcontroller 48 and transmitted to the database 74 (Block 86) via the network interface 68 and the network 70. The transmitted waveform may then be compared (such as by utilizing a processor that is not shown in FIG. 2) to the waveforms in the library of the database 74 (Block 88) for determining the type of alarm, the device generating the alarm, an alarm level, or combinations thereof.

Designation of alarm levels may vary, but according to the illustrative embodiment of the present invention, the levels may be binary: emergency and minor. That is the digital waveform may be associated with a designation that the alarm indicates a need for immediate attention ("Emergency" branch of the Decision Block 90) or that the alarm indicates a need that does not require immediate attention ("Minor" branch of the Decision Block 90). Emergency level alarms may include, for example, sudden drop of blood pressure or blood oxygen level; minor level alarms may include, for example, low battery power level or IV fluid level warning. For emergency level alarms ("Emergency" branch of Decision Block 90), hospital staff may be alerted as to the emergency nature of the alarm (Block 92). For minor level alarms ("Minor" branch of Decision Block 90), the system may be configured to mute the alarm and set a reminder for hospital staff to investigate the alarm at an opportune time (Block 94).

According to some embodiments, the website referenced previously may be used to facilitate reporting alarm levels. For example, the website may present a floor plan of the hospital rooms within a unit. The second detector 78 may be identified on the floor plan (for example, using the unique identifier). The system may then indicate, on the floor plan representation on the website, that the vital signs monitor 26 (FIG. 6) issued an alarm level that was determined to be minor in nature.

It would be readily understood by those of ordinary skill in the art having the benefit of the disclosure made herein that this description of the illustrated embodiment of FIG. 7 is exemplary in nature, that any illustrated detector 76, 80, 82 or non-illustrated detector may be used to detect the alarm, and that various arrangements and types of alarm levels are possible. Additionally, it would be further understood that use of waveforms may require additional processing of the sound. That is, the waveform will need to be isolated from other detected sounds: other alarms, people talking, footsteps, knocking at doors, phones ringing and so forth. As such, the microcontroller 48 may require greater processing capacity, higher energy demand, and so forth.

Figure 8:
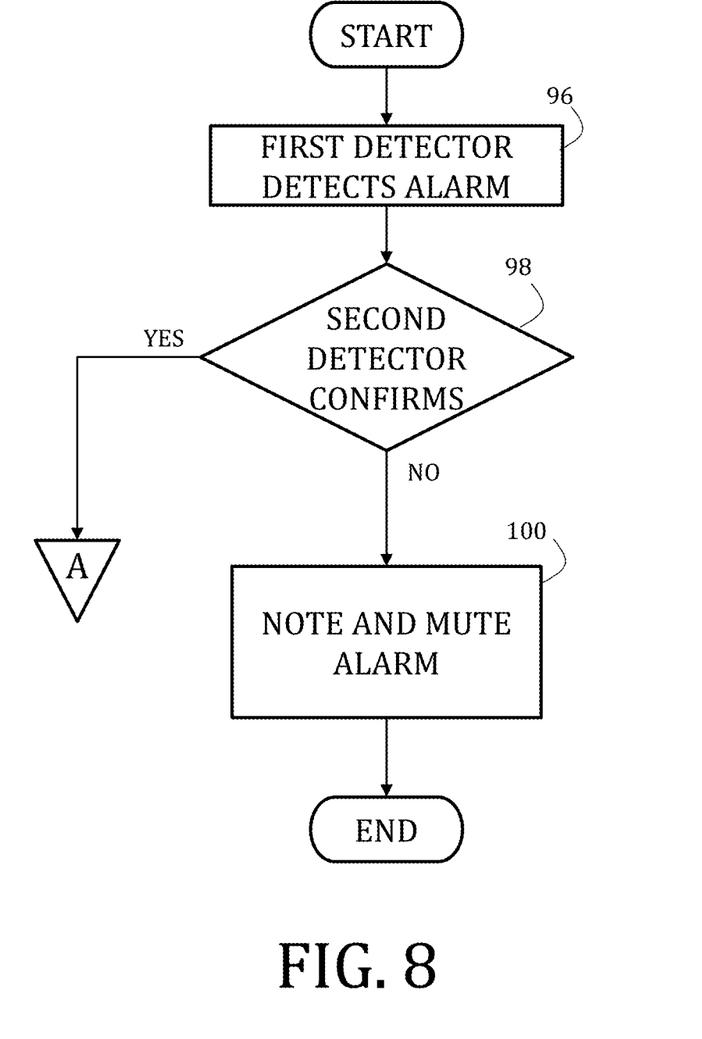
FIG. 8 is a flowchart illustrating a method of managing patient alert systems according to another embodiment of the present invention.

Adding reference now to FIG. 8 with continue reference to FIGS. 2, 6, and 7, a method of detecting, triaging, and communicating audio alarms associated with a medical sensor according to an embodiment of the present invention is shown. At start, the microphone 46, 54, 56 of the first detector 76 detects an alarm (Block 96). The microcontroller 48 converts the alarm's sound from an analog signal to a digital waveform and transmits the digital waveform to the networked devices (including, for example, the server 72 or database 74) by way of the network interface 68 and the network 70.

Prior to correlating the digital waveform to the library comprising the plurality of waveforms, the system will inquire as to whether the second detector 80 confirms (i.e., also detected) the alarm ("Yes" branch of Decision Block 98). In that instance, the process may return to Block 86 of FIG. 6 for evaluation of the alarm. If the alarm is not confirmed by the second detector 80 ("No" branch of Decision Block 98), then the system may be configured to mute the alarm and set a reminder for hospital staff to investigate the alarm at an opportune time (Block 100).

As described herein according to the various embodiments of the present invention, the device and system for detecting, locating, and processing alarms from medical devices facilitate triaging of alarms and may reduce the likelihood of alarm fatigue. Moreover, the devices and systems are configured to interface with virtually any medical device without need for particular outputs or specific interfacing hardware.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A system for monitoring a medical device alarm, the system comprising:
   a plurality of detectors, each detector of the plurality comprising:
      a microphone configured to receive a sound of an alarm;
      a microcontroller configured to determine an alarm pattern from the sound and to compare the determined alarm pattern to a plurality of patterns stored in a memory to identify a cause of the alarm; and
      a network interface configured to transmit the cause of the alarm; and
   a server configured to receive the cause of the alarm and provide notification of the cause of the alarm,
   wherein the server is further configured to compare the determined alarm pattern of a first detector of the plurality to the determined alarm pattern of a second detector of the plurality.

2. The system of claim 1, wherein each detector of the plurality is operably coupled to a different medical device within a patient room.

3. The system of claim 1, wherein each detector of the plurality is operably coupled to a different medical device of different patient rooms.

4. The system of claim 1, wherein each detector of the plurality further comprises:
   a plurality of microphones positioned in a two- or three-dimensional arrangement and the microcontroller is further configured to triangulate a source of the alarm based on the arrangement of the plurality of microphones.

5. The system of claim 1, wherein the detector further comprises:
   a power source.

6. The system of claim 1, wherein the server is configured to host a website for providing the cause of the alarm.

7. The system of claim 1, wherein the server is configured to provide the cause of the alarm to a hospital staff call system, a computing device, or a telecommunication system.

8. The system of claim 1 wherein the plurality of detectors comprises a first detector and a second detector, wherein when an alarm is detected by the microphone of the first detector the server inquires as to whether the microphone of the second detector also detected the same alarm, and if confirmed the server uses the relative location of the first and second detectors to triangulate the source of the alarm.

9. The system of claim 1 wherein the plurality of patterns stored in the memory comprise a plurality of digital waveforms, and further wherein a digital waveform identifies at least one of a type of alarm, a device generating the alarm, and an alarm level.

10. The system of claim 9 wherein the alarm level is one of an emergency alarm and a minor alarm.

11. The system of claim 10 wherein the server is configured to alert a hospital staff as to the emergency nature of the alarm when the alarm level is an emergency alarm, and to mute the alarm and set a reminder for hospital staff to investigate the alarm at an opportune time when the alarm level is a minor alarm.

12. The system of claim 1 wherein the plurality of detectors comprises a first detector and a second detector, wherein when an alarm is detected by the microphone of the first detector the server inquires as to whether the microphone of the second detector also detected the same alarm, and wherein the system is configured to mute the alarm and set a reminder for hospital staff to investigate the alarm at an opportune time if the second detector does not confirm the alarm.

13. The system of claim 1, wherein at least one of the plurality of detectors is not operably connected to a medical device within a patient room.

14. The system of claim 1, wherein at least one of the plurality of detectors is not operably connected to a medical device and is located outside a patent room containing at least one medical device that can be the source of the sound of the alarm.

15. A system for monitoring at least one of a plurality of alarms, the system comprising:
    a plurality of detectors, each detector of the plurality comprising:
        a microphone configured to receive a sound of an alarm;
        a microcontroller configured to determine an alarm pattern from the sound and to compare the determined alarm pattern to a plurality of patterns stored in a memory to identify a cause of the alarm; and
        a network interface configured to transmit the cause of the alarm; and
    a server configured to receive the cause of the alarm and provide notification of the cause of the alarm,
    wherein the server is further configured to compare the determined alarm pattern of a first detector of the plurality to the determined alarm pattern of a second detector of the plurality.

16. The system of claim 15, wherein each detector of the plurality is operably coupled to a different device having an alarm and located within a room.

17. The system of claim 15, wherein each detector of the plurality is operably coupled to a different device having an alarm and with at least one of the devices having an alarm located in a different room.

18. The system of claim 15, wherein each detector of the plurality further comprises:
    a plurality of microphones positioned in a two- or three-dimensional arrangement and the microcontroller is further configured to triangulate a source of the alarm based on the arrangement of the plurality of microphones.

19. The system of claim 15, wherein the server is configured to host a website for providing the cause of the alarm.

20. The system of claim 15, wherein the server is configured to provide the cause of the alarm to a staff call system, a computing device, or a telecommunication system.

\* \* \* \* \*